United States Patent [19]
Chung et al.

[11] Patent Number: 5,683,569
[45] Date of Patent: Nov. 4, 1997

[54] METHOD OF SENSING A CHEMICAL AND SENSOR THEREFOR

[75] Inventors: Young Sir Chung, Gilbert; Keenan L. Evans, Tempe, both of Ariz.

[73] Assignee: Motorola, Inc., Schaumburg, Ill.

[21] Appl. No.: 608,357

[22] Filed: Feb. 28, 1996

[51] Int. Cl.$^6$ .................................................. G01N 27/26
[52] U.S. Cl. .................. 205/775; 204/416; 257/253; 257/467; 257/469; 422/82.01; 422/82.02; 422/82.03; 436/149; 436/150; 436/151; 436/153
[58] Field of Search .................. 205/775; 204/416; 257/253, 467, 469; 422/82.01, 82.02, 82.03, 98; 436/149, 150, 151, 153

[56] References Cited

U.S. PATENT DOCUMENTS

| | | | |
|---|---|---|---|
| 3,999,122 | 12/1976 | Winstel et al. | 422/82.02 |
| 4,514,263 | 4/1985 | Janata | 204/416 |
| 5,386,715 | 2/1995 | Evans et al. | 73/31.05 |
| 5,576,563 | 11/1996 | Chung | 257/253 |

OTHER PUBLICATIONS

Wilson et al., Review of Physical Instruments, "Field–Effect Probe for Work Function Measurements", May 1989, pp. 886–887.

Lundström et al., Applied Physics Letters, "A Hydrogen–Sensitive MOS Field–Effect Transistor", Jan. 15, 1975, vol. 26, No. 2, pp. 55–57.

*Primary Examiner*—Bruce F. Bell
*Attorney, Agent, or Firm*—George C. Chen

[57] ABSTRACT

A sensor (10) includes a gate electrode (20) overlying a channel region (34). A gap (22) between the gate electrode (20) and the channel region (34) allows a surface (28) of the gate electrode (20) to be exposed to a chemical. Upon exposure to the chemical, a surface potential or an electrical impedance of the gate electrode (20) may change. Comparing the changes in surface potential versus the changes in electrical impedance provides a method to distinguish between similar chemical species and also to extend the detection range of the sensor (10).

20 Claims, 1 Drawing Sheet

METHOD OF SENSING A CHEMICAL AND SENSOR THEREFOR

BACKGROUND OF THE INVENTION

This invention relates, in general, to semiconductor devices, and more particularly, to sensors.

Chemical sensors are used to detect or monitor the presence of a particular chemical species and its concentration level for personal safety, process control, health, and environmental awareness. The development of metal-oxide-semiconductor (MOS) chemical sensors has been a topic of great interest because MOS chemical sensors are portable, are inexpensive, and are relatively simple to fabricate compared to other types of chemical sensors. However, MOS chemical sensors typically have poor selectivity between similar chemical species. Furthermore, MOS chemical sensors are generally limited to measuring a narrow range of chemical concentrations.

Accordingly, a need exists for a method of distinguishing between similar chemical species and detecting a wide range of concentrations for a specific chemical species. The method should use a sensor that is accurate, cost-effective, portable, and capable of being manufactured using existing semiconductor fabrication techniques.

DETAILED DESCRIPTION OF THE DRAWINGS

Figure 1:
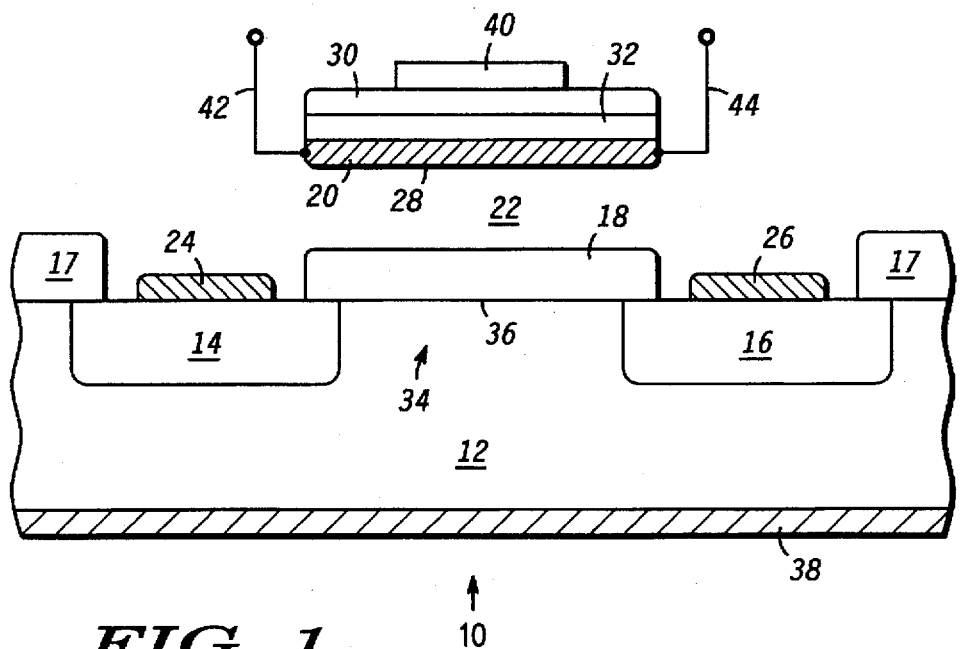
FIG. 1 illustrates a partial cross-sectional view of an embodiment of a sensor in accordance with the present invention.

Turning to the figures for a more detailed description, FIG. 1 illustrates a partial cross-sectional view of an embodiment of a sensor or chemical probe impedance field effect transistor (CPIFET) 10. Sensor 10 includes a semiconductor substrate 12, which is comprised of a semiconductor such as, for example, n-type silicon or gallium arsenide. A dielectric layer 17 is formed or grown over semiconductor substrate 12 using oxidation or other techniques known in the semiconductor art. A source region 14 and a drain region 16 are disposed or formed in semiconductor substrate 12 and adjacent to channel region 34 by using ion implantation techniques or diffusion processes. A channel region 34 is located between source region 14 and drain region 16. The doping level of channel region 34 can be modulated by ion implantation or diffusion processes.

A source contact 24 and a drain contact 26 are formed overlying source region 14 and drain region 16, respectively, to provide a source voltage and a drain voltage, respectively, for sensor 10. Source contact 24 and drain contact 26 can be comprised of a metal such as aluminum silicon and can be formed by using metal deposition and etching processes or silicide processes known in the art.

A gate insulator 18 is provided on a surface 36 of semiconductor substrate 12 and overlying channel region 34. Gate insulator 18 is an electrical insulator between a gate electrode 20 and channel region 34. Gate insulator 18 can be comprised of silicon oxide, which is thermally grown over surface 36 of semiconductor substrate 12, or gate insulator 18 can be comprised of silicon nitride or silicon oxynitride, which is deposited over surface 36 using a chemical vapor deposition technique.

A metal layer 38 is deposited over a back surface of semiconductor substrate 12 using a sputtering, evaporating, or electroplating technique. Metal layer 38 is a conventional metal structure that provides a substrate bias voltage to sensor 10 and can be comprised of titanium, nickel, silver, gold, or platinum.

A gate electrode 20 is disposed above channel region 34 to provide an opening or gap 22 of about 0.01 to 20 microns between gate insulator 18 and a surface 28 of gate electrode 20. Gate electrode 20 is supported over channel region 34 and is formed from a chemically sensitive and electrically conducting material using semiconductor processing techniques known in the art. For example, gate electrode 20 can be a structure similar to a cantilever, diaphragm, or air bridge. Gate electrode 20 is comprised of a sensing material whose composition is dependent upon the desired chemical species to be detected, sensed, or monitored by sensor 10.

For example, if gate electrode 20 is comprised of an alloy of gold and palladium, gate electrode 20 can sense or chemically react with both phosphine and arsine. Other suitable materials for gate electrode 20 include, but are not limited to, a metal oxide such as, for example, tin oxide ($SnO_2$) or titanium oxide ($TiO_2$), or a thin layer of a noble or transition metal such as, for example, platinum. It is understood that the material used for gate electrode 20 can also be doped to improve the sensitivity and selectivity of gate electrode 20.

The chemical reactivity or the kinetics of adsorption and desorption of gate electrode 20 are dependent upon the temperature of gate electrode 20. Therefore, a heater 30 is provided in close proximity to gate electrode 20 to uniformly control the temperature of gate electrode 20 and to improve the response time and sensitivity of sensor 10. In the embodiment of FIG. 1, heater 30 is located above gate electrode 20 and is comprised of an electrically resistive material such as, for example, polysilicon, a nickel-chrome alloy, heavily-doped silicon, a tantalum alloy, or platinum.

If gate electrode 20 is comprised of a gold and palladium alloy and is designed to detect phosphine or arsine, heater 30 heats gate electrode 20 to approximately 80–120 degrees Celsius (°C.) to improve the sensitivity of sensor 10 for detecting phosphine or arsine. Heater 30 can also be used to heat gate electrode 20 to approximately 180°–220° C. to refresh or regenerate gate electrode 20 and to improve its recovery time after gate electrode 20 has sensed the phosphine or arsine. Heater 30 can also be used to modify or adjust the temperature coefficient of resistivity for gate electrode 20 in order to maximize the sensitivity of sensor 10.

An insulator 32 is provided or disposed between gate electrode 20 and heater 30 to provide electrical isolation therebetween. Insulator 32 is comprised of a nitride, an oxide, or an oxynitride. A thinner insulator 32 provides a more efficient heating scheme for gate electrode 20 and reduces the power consumption of sensor 10. Therefore, the thickness of insulator 32 is chosen to minimize power consumption while maintaining electrical isolation and mechanical stability.

A temperature sensor 40, as known in the art, is provided in close proximity to heater 30 to monitor the temperature of heater 30. In the embodiment of FIG. 1, temperature sensor 40 is located above heater 30.

Gap 22 enables or permits a fluid or a gas (not shown) to contact surface 28 of gate electrode 20 by passing between gate insulator 18 and gate electrode 20. In one embodiment, the fluid or the gas includes a chemical that chemically reacts with surface 28, and this chemical reaction changes both a surface potential and an electrical impedance of gate electrode 20. The surface potential of gate electrode 20 is also known in the art as a work function and is a function of the surface polarity of gate electrode 20 due to the exposure to the chemical being sensed. The electrical impedance of gate electrode 20 is also known in the art as a resistance, is a function of the diffusivity of the chemical on and into surface 28, and is also a function of the surface states of gate electrode 20, which are altered by the chemical exposure.

In an alternative embodiment, the chemical reaction between surface 28 and the gas or fluid may only change the surface potential of gate electrode 20 while the electrical impedance of gate electrode 20 remains substantially constant or vice versa. As explained in more detail hereinafter, the composition of gate electrode 20, the specific chemical species reacting with gate electrode 20, and the concentration of the specific chemical species being sensed by sensor 10 determine whether only the surface potential, only the electrical impedance, or both the surface potential and the electrical impedance change.

Under operation, gate electrode 20, source contact 24, and drain contact 26 are typically each biased at a substantially constant voltage. The substantially constant voltage of gate electrode 20 controls a magnitude of a current in channel region 34. However, when the surface potential of gate electrode 20 changes as a result of a reaction with a chemical in gap 22, the threshold voltage of the transistor or sensor 10 is altered, and thus, the magnitude of the current in channel region 34 is also modified. Therefore, the modulation in surface potential changes the current in channel region 34 while gate electrode 20, source contact 24, and drain contact 26 each remain biased at a substantially constant voltage.

When the variation in the current in channel region 34 is detected or measured through source contact 24 and drain contact 26, a change in the surface potential of gate electrode 20 can be determined from the measured current variation using techniques known in the art. From the change in surface potential, the change in concentration of a chemical in gap 22 can be determined.

As illustrated in the embodiment of FIG. 1, electrodes or electrical connections 42 and 44 are coupled to gate electrode 20. While gate electrode 20 is biased at the substantially constant voltage, electrical connections 42 and 44 provide the ability to determine or measure the electrical impedance or resistance of gate electrode 20.

For example, electrical connections 42 and 44 can be used to force a substantially constant current across gate electrode 20, which is a resistor. Then, electrical connections 42 and 44 can also be used to measure the voltage drop across gate electrode 20. The electrical impedance or resistance of gate electrode 20 is calculated by dividing the measured voltage drop by the substantially constant current forced across gate electrode 20. While the substantially constant current is forced across gate electrode 20, the measured voltage across gate electrode 20 may change when the resistance of gate electrode 20 is altered by a reaction with a desired chemical. Therefore, a change in the measured voltage across gate electrode 20 is used to determine a change in the resistance across gate electrode 20, which is used to indicate a change in the concentration of the chemical.

To provide a more accurate measurement of the resistance of gate electrode 20, a four terminal measurement technique can be used. For example, electrical connections 42 and 44 and two additional electrical connections (not shown) can be coupled to gate electrode 20. In this example, the two additional electrical connections force a substantially constant current across gate electrode 20 while electrical connections 42 and 44 measure a voltage drop across gate electrode 20.

In summary, variations in the surface potential of gate electrode 20 and variations in the electrical impedance of gate electrode 20 are measured to determine the concentration of a specific chemical species. The two measurements can also be used to extend the concentration measurement range of sensor 10 as explained hereinafter.

Figure 2:
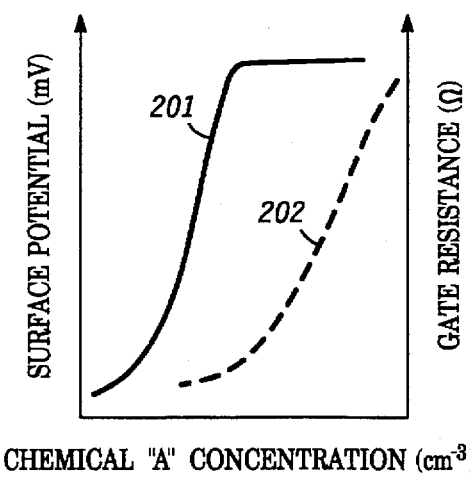
FIGS. 2 and 3 portray embodiments of the operation of the sensor in accordance with the present invention.

FIG. 2 portrays an embodiment of the operation of sensor 10. An abscissa or x-axis of a graph in FIG. 2 represents a concentration of a chemical "A" in gap 22 that is chemically reactive with surface 28 of gate electrode 20. A first ordinate or y-axis of the graph in FIG. 2 represents a magnitude of a surface potential for gate electrode 20. The x-axis has units of per centimeters cubed ($cm^{-3}$) while the first y-axis has units of millivolts (mV). Accordingly, a curve 201 relates or plots the concentration of chemical species "A" in gap 22 versus the surface potential of gate electrode 20. Curve 201 shows that an increase in the concentration of chemical species "A" causes an increase in the surface potential of gate electrode 20. As discussed previously, the surface potential of gate electrode 20 is calculated from a measurement of the current in channel region 34.

The graph in FIG. 2 also has a second ordinate or y-axis that represents a gate resistance or electrical impedance of gate electrode 20. The second y-axis has units of ohms ($\Omega$). A curve 202 shows that the gate resistance of gate electrode 20 increases as the concentration of chemical species "A" in gap 22 increases.

By examining curves 201 and 202 of FIG. 2, one skilled in the art will understand that the measurements of surface potential and electrical resistance are used in combination to extend the concentration measurement range of sensor 10. More specifically, in this particular embodiment represented in FIG. 2, smaller concentrations of chemical species "A" that react with gate electrode 20 significantly change the surface potential or work function of gate electrode 20 but do not significantly affect the resistance of gate electrode 20. As the change in surface potential saturates at larger concentrations of chemical species "A", the changes in the resistance of gate electrode 20 becomes more significant. Therefore, in the embodiment of FIG. 2, the variation in surface potential is used to detect or monitor lower concentrations of chemical species "A" while the variation in gate resistance is used to detect or monitor higher concentrations of chemical species "A".

Thus, sensor 10 can be used to detect or monitor a chemical over a wide range of concentrations. This improved sensing range is provided with reduced power consumption compared to the prior art. A single heater 30 instead of a plurality of heaters is used to regulate the operating temperature for measuring both the change in resistance and the change in surface potential. Accordingly, sensor 10 is suitable for portable applications because of its reduced power consumption.

Figure 3:
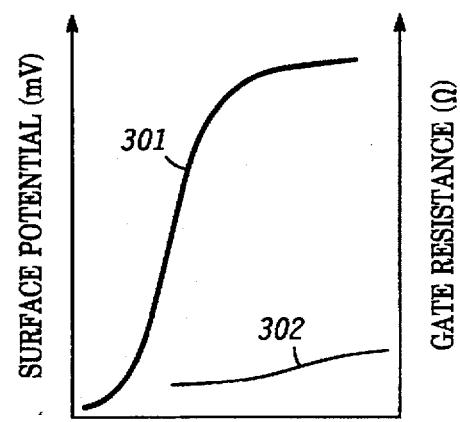

FIG. 3 portrays another embodiment of the operation of sensor 10. A graph in FIG. 3 has an abscissa or x-axis that represents a concentration of a chemical species "B" in gap 22 and also has a first ordinate or y-axis that represents a surface potential of gate electrode 20. The units for the x-axis and the first y-axis are $cm^{-3}$ and mV, respectively. Accordingly, a curve 301 plots the concentration of chemical species "B" versus the surface potential of gate electrode 20, wherein a larger or higher chemical concentration results in a larger or higher surface potential.

The graph in FIG. 3 also has a second ordinate or y-axis that represents a resistance of gate electrode 20 and has units of Ω. Accordingly, a curve 302 relates the concentration of chemical species "B" to the gate resistance of gate electrode 20, wherein a higher chemical concentration produces a higher gate resistance.

It is assumed that chemical species "A" of FIG. 2 is similar in composition to chemical species "B" of FIG. 3. Accordingly, similar to chemical species "A", chemical species "B" also reacts with gate electrode 20. As depicted in FIG. 3, lower or smaller concentrations of chemical species "B" significantly change or modify the surface potential of gate electrode 20 but do not significantly alter the resistance of gate electrode 20. Higher concentrations of chemical species "B" begin to significantly change the resistance of gate electrode 20, but the surface potential signal of gate electrode 20 becomes saturated at higher concentrations of chemical species "B".

The composition of gate electrode 20 may react with two similar chemicals species, such as species "A" and "B". However, the effects of the two similar chemical species on surface potential and resistance may be different, and this difference can be utilized to distinguish between the two similar chemical species. For example, when comparing the graphs of FIGS. 2 and 3, one skilled in the art will recognize that the surface potential of gate electrode 20 responds in a similar manner to lower concentrations of both chemical species "A" and "B". However, one skilled in the art will also recognize that the resistance of gate electrode 20 changes more quickly when gate electrode 20 is subjected or exposed to higher concentrations of chemical species "A" compared to chemical species "B". Accordingly, the surface potential variations and gate resistance variations can be compared and contrasted to distinguish between two similar chemical species "A" and "B".

Therefore, in accordance with the present invention, it is apparent there has been provided an improved sensor that overcomes the disadvantages of the prior art. The present invention eliminates the limitations in detection ranges and inaccuracies of prior art sensors. The present invention provides multi-sensing capabilities for extending the detection range of chemical concentrations and for enhancing sensor response time, sensitivity, and selectivity. The present invention uses surface potential properties to measure lower concentrations of a chemical species and uses resistance properties to measure higher concentrations of the same chemical species.

The present invention also uses surface potential and resistance properties to determine the presence of a particular chemical species and to distinguish between two similar chemical species. Furthermore, the present invention is also suitable for portable applications because of its reduced power consumption. Moreover, the present invention is cost-effective and can be manufactured using conventional semiconductor fabrication techniques.

While the invention has been particularly shown and described with reference to preferred embodiments, it will be understood by those skilled in the art that changes in form and detail may be made without departing from the spirit and scope of the invention. For instance, while the graphs of FIGS. 2 and 3 plot chemical concentration versus surface potential, it is understood that a similar plot of chemical concentration versus channel current can also be used. Accordingly, the disclosure of the present invention is not intended to be limiting, but instead, is intended to be illustrative of the scope of the invention, which is set forth in the following claims.

We claim:

1. A method of sensing a chemical comprising the steps of:
   providing a sensing material;
   detecting a surface potential of the sensing material;
   detecting an electrical impedance through the sensing material; and
   comparing the surface potential to the electrical impedance to determine a presence of the chemical.

2. The method according to claim 1 further comprising the step of providing a transistor wherein the sensing material is a gate electrode for the transistor.

3. The method according to claim 1 further comprising the step of providing a transistor comprised of a semiconductor substrate wherein the semiconductor substrate has a channel and wherein the surface potential is calculated from a magnitude of a current in the channel.

4. The method according to claim 1 wherein the step of detecting the surface potential includes detecting a change in the surface potential.

5. The method according to claim 1 wherein the step of detecting the surface potential includes measuring a current.

6. The method according to claim 1 wherein the step of detecting the electrical impedance includes detecting a change in the electrical impedance.

7. The method according to claim 1 further comprising the step of exposing the sensing material to the chemical prior to the step of comparing the surface potential to the electrical impedance and wherein the step of comparing the surface potential to the electrical impedance includes determining a concentration of the chemical.

8. A method of sensing a chemical comprising the steps of:
   providing a transistor having a gate electrode overlying a channel region;
   using the gate electrode to control a current in the channel region;
   measuring a resistance of the gate electrode;
   measuring a magnitude of the current; and
   comparing the resistance of the gate electrode to the magnitude of the current to sense the chemical.

9. The method according to claim 8 further comprising the step of exposing the transistor to a gas comprised of the chemical.

10. The method according to claim 8 further comprising the step of exposing the transistor to a liquid comprised of the chemical.

11. The method according to claim 8 wherein the step of measuring the resistance of the gate electrode includes measuring a variation in the resistance of the gate electrode.

12. The method according to claim 8 wherein the step of measuring the magnitude of the current includes measuring a variation in the magnitude of the current.

13. The method according to claim 8 wherein the step of measuring the magnitude of the current includes calculating a surface potential of the gate electrode.

14. The method according to claim 13 wherein the step of comparing the resistance of the gate electrode to the magnitude of the current includes comparing the resistance of the gate electrode to the surface potential of the gate electrode.

15. The method according to claim 8 wherein the step of comparing the resistance of the gate electrode to the magnitude of the current includes distinguishing between a first chemical and a second chemical.

16. The method according to claim 8 wherein the step of providing the transistor includes providing the transistor having a source region and a drain region wherein the channel region is located between the source region and the drain region, and wherein the step of using the gate electrode to control the current in the channel region includes the steps of:

biasing the gate electrode with a first substantially constant voltage;

biasing the source region with a second substantially constant voltage; and biasing the drain region with a third substantially constant voltage.

17. A sensor comprising:

a semiconductor substrate;

a channel in the semiconductor substrate;

a gate electrode overlying the channel, wherein a gap exists between the gate electrode and the semiconductor substrate;

a first electrical connection coupled to the gate electrode; and a second electrical connection coupled to the gate electrode.

18. The sensor according to claim 17 wherein the semiconductor substrate, the channel, and the gate electrode form a transistor and wherein the first and second electrical connections measure a resistance in the gate electrode.

19. The sensor according to claim 17 further comprising a heater coupled to the gate electrode.

20. The sensor according to claim 19 further comprising a temperature sensor coupled to the heater.

* * * * *